United States Patent [19]

Motomura et al.

[11] Patent Number: 5,434,416

[45] Date of Patent: Jul. 18, 1995

[54] METHOD AND APPARATUS FOR RECONSTRUCTING SPECT IMAGE BY UTILIZING TWO SEPARATE RECONSTRUCTION FILTER FUNCTIONS

[75] Inventors: Nobutoku Motomura; Takashi Ichihara, both of Tochigiken, Japan

[73] Assignee: Kabushiki Kaisha Toshiba, Kawasaki, Japan

[21] Appl. No.: 217,102

[22] Filed: Mar. 24, 1994

[30] Foreign Application Priority Data

Mar. 24, 1993 [JP] Japan ................... 5-065213

[51] Int. Cl.[6] ............ A61B 6/00; G06F 19/00; G01T 1/166
[52] U.S. Cl. .................. 250/369; 250/363.04; 364/413.21
[58] Field of Search ............ 250/363.03, 363.04, 250/369; 364/413.19, 413.21

[56] References Cited

U.S. PATENT DOCUMENTS

| 4,729,100 | 3/1988 | Tsujii | 364/413.21 |
| 5,324,946 | 6/1994 | Ichihara et al. | 250/363.04 |

FOREIGN PATENT DOCUMENTS 57-69268 4/1982 Japan ................ 250/363.04

OTHER PUBLICATIONS

G. T. Herman, et al., Convolution Reconstruction Techniques For Divergent Beams, Compt. Biol, Med, 1976, vol. 6, pp. 259–271.

*Primary Examiner*—Carolyn E. Fields
*Assistant Examiner*—Edward J. Glick
*Attorney, Agent, or Firm*—Oblon, Spivak, McClelland, Maier, & Neustadt

[57] ABSTRACT

A method and an apparatus for reconstructing SPECT image capable of improving the SPECT image resolution. The apparatus includes: a detector, including a fan-beam collimator, for detecting gamma ($\gamma$) rays emitted from a radio isotope injected into a biological body; a rotation unit for effecting relative rotation between the biological body and the detector about a center of rotation to thereby acquire projection data from a different direction; a first reconstructing unit for convoluting the projection data obtained from the detector, by a first convolution function, and for back-projecting the convoluted projection data to a specific region which lies in a sufficiently close vicinity of the detector; a second reconstructing unit for convoluting the projection data by a second convolution function, and for back-projecting the secondly convoluted projection data to another specific region; and display means for displaying thereon a distribution image reconstructed by the first and second reconstructing units.

10 Claims, 8 Drawing Sheets

METHOD AND APPARATUS FOR RECONSTRUCTING SPECT IMAGE BY UTILIZING TWO SEPARATE RECONSTRUCTION FILTER FUNCTIONS

BACKGROUND OF THE INVENTION

1. Technical Field

The present invention relates to a method and apparatus for constructing a SPECT (single photon emission computed tomography) image that is a three-dimensional distribution image of a radio isotope (RI) which is injected into a biological body under medical examination, by detecting γ (gamma) rays emitted from the injected radio isotope (RI).

2. Background Art

Conventionally, there are available a computer tomography (CT) apparatus and a single photon emission computed tomography (SPECT) apparatus as one which reconstructs image by detecting radiation.

In the CT apparatus, there are provided an X-ray source and a group of detecting elements arranged in a geometric position where the X-ray source lies in a focus point of an X-ray fan beam. The X-ray source and the detecting elements are rotated around the longitudinal axis of the biological body so that an X-ray permeated through the biological body is detected by the group of the detecting elements so as to acquire projected data. Then, X-ray absorption distribution is image-reconstructed in accordance with the projected data thus acquired.

In SPECT apparatus, in order to detect γ rays emitted from a radio isotope (RI) injected into a patient, there are provided a fan-beam collimator constructing a hypothetical focus, a scintillation detector which converts selectively transmitted γ rays into light rays so as to be detected thereby. The fan-beam collimator and the scintillation detector constitutes a gamma camera. The distribution of radio isotope (RI) is image-reconstructed in accordance with the projected data acquired by the gamma camera, in a manner that the absorption of the γ rays are neglected.

In either CT or SPECT apparatus, there is often utilized a filtered back projection technique. An example for the filtered back projection technique, there is a publication entitled "CONVOLUTION RECONSTRUCTION TECHNIQUES FOR DIVERGENT BEAMS" by G. T. Herman et al., Comput. Biol. Med. Vol. 6;1976, pages 259-271,". In this above publication, the X-ray fan beam is exposed to the patient from the X-ray source which rotates around the patient. The X-ray transmitted through the patient is detected by a detecting unit in which a plurality of the detecting elements are arranged in a linear or circular arc shape. Projection data thus detected are corrected by a filtering process. Thereafter, the filtered data are backprojected to entire effective field of view along an X-ray beam so as to reconstruct an X-ray CT image. In this case, the X-ray source lies in the focus, so that image information from all directions of 360° are regarded equivalent in a relative manner.

However, in a case where the image is reconstructed by employing the filtered backprojection technique in the SPECT using the fan-beam collimator, a spatial resolution near the collimator is comparatively good while the spatial resolution deteriorates as a region is away from the collimator. In other words, an RI distribution located far away from the collimator does not sufficiently contribute to information on the projection data, thus resolution of the image thus constructed from the far-away region being very deteriorated.

SUMMARY OF THE INVENTION

In view of the foregoing drawbacks, it is therefore an object of the present Invention to provide a method and an apparatus for reconstructing SPECT image capable of improving the SPECT image resolution.

To achieve the object, there is provided a nuclear medical apparatus, such as a SPECT apparatus, in which a distributed image of radio isotopes injected into a biological body under medical examination is reconstructed, the apparatus comprising: detector means, including a fan-beam collimator, for detecting in a fan-beam form, gamma (γ) rays emitted from the radio isotope, so that gamma ray projection data for the biological body is obtained; means for effecting relative rotation between the biological body and the detector means about a center of rotation to thereby acquire projection data from a different direction; first reconstructing means for convoluting the projection data obtained from the detector means, by a first convolution function, and for back-projecting the first convoluted projection data to a specific region which lies in a sufficiently close vicinity of the detection means; second reconstructing means for convoluting the projection data by a second convolution function, and for back-projecting the secondly convoluted projection data to another specific region; and display means for displaying thereon a distribution image reconstructed by the first and second reconstructing means.

To achieve the object, there is also provided a method for reconstructing SPECT image comprising the steps of:(i) detecting gamma-rays emitted from a radio isotope so as to obtain projection data, by detecting means in a fan-beam form around a biological body with respect to a rotation center for 360°; (ii) firstly performing convolution operation between the projection data and a first convolution function, and then backprojecting a result of the convolution operation in a manner that a backprojecting region corresponds to an effective field which lies within sufficiently close vicinity to the detecting means; (iii) secondly performing convolution operation between the projection data and a second convolution function, and then backprojecting a result of the convolution operation in a reconstruction region; and (iv) obtaining the SPECT image in accordance with backprojection results obtained from step (ii) and step (iii).

BRIEF DESCRIPTION OF THE DRAWINGS

These and other objects, features and advantages of the present invention will become more apparent from the following description of the preferred embodiment taken in conjunction with the accompanying drawings, in which.

DETAILED DESCRIPTION OF THE PREFERRED EMBODIMENTS

Features of the present invention will become apparent in the course of the following description of exemplary embodiments which are given for illustration of the invention and are not intended to be limiting thereof. Embodiments of the present invention will now be described with reference to the drawings.

Figure 1:
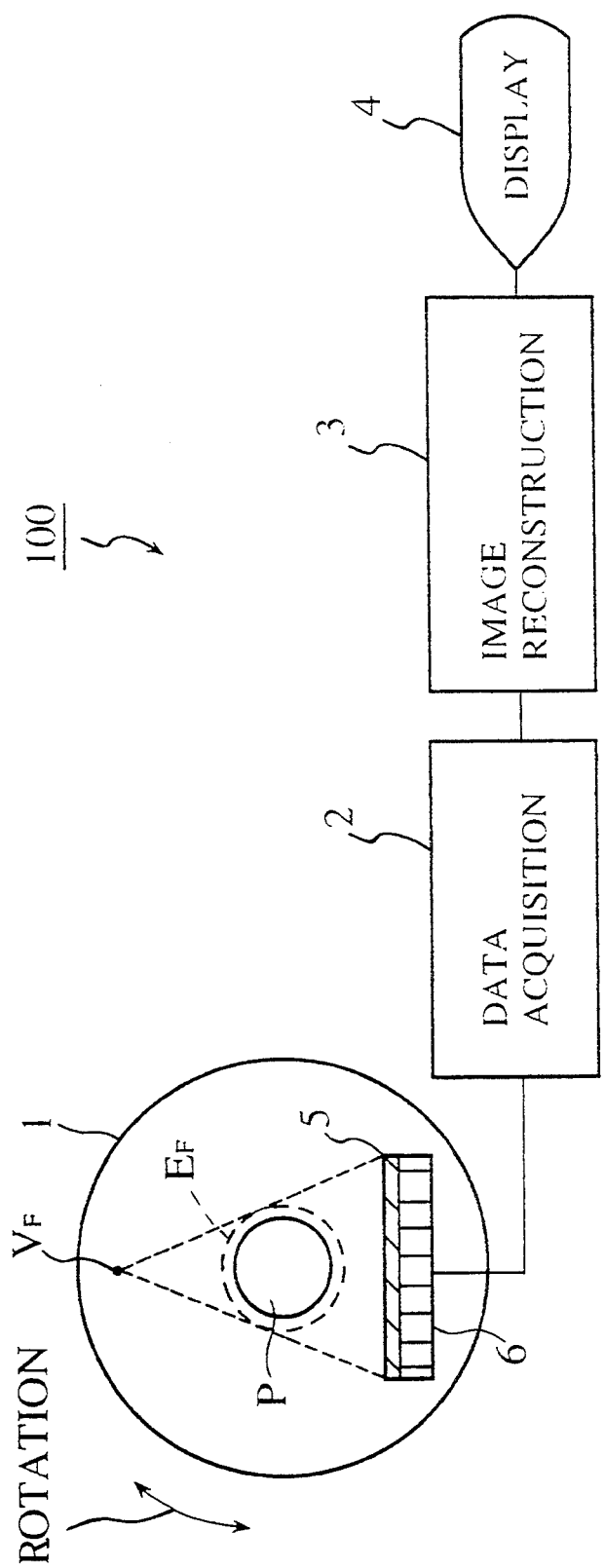
FIG. 1 is a schematic block diagram for representing an overall arrangement of a SPECT image reconstructing apparatus according to the present invention.

FIG. 1 is a schematic block diagram for representing an overall arrangement of a nuclear medical examination apparatus such as a single photon emission computed tomography apparatus (hereinafter simply referred to as a SPECT imaging apparatus) 100 according to a preferred embodiment of the present invention.

SPECT imaging apparatus 100 comprises a gantry 1 for providing a space for a biological body to be examined therein, a data acquisition unit 2, an image reconstruction unit 3, a display unit 4, a fan-beam collimator 5 and a gamma camera 6.

In gantry 1, the gamma camera 6 equipped with the fan beam collimator 5 can be rotated with respect to the biological body P under medical examination as a rotating center in order to detect γ (gamma) rays irradiated from a radio isotope injected into the biological body P in an omnidirection (360°).

Alternatively, more than one gamma camera may be employed and pivoted around the rotating center.

Projection data derived from a gamma camera 6 rotatably fixed on gantry 1, is acquired by data acquisition unit 2. The projection data derived from the gamma camera 6 is first filter-processed in data acquisition unit 2, in which the filtering process is divided into the two separate processes which will be described later. Then, two separate data convoluted by the respective convolution functions (also referred to as reconstruction filtering functions) are back-projected respectively in the image reconstruction unit 3. Thereafter, those respective back-projected data are summed up so as to obtain final reconstruction images.

Figure 2:
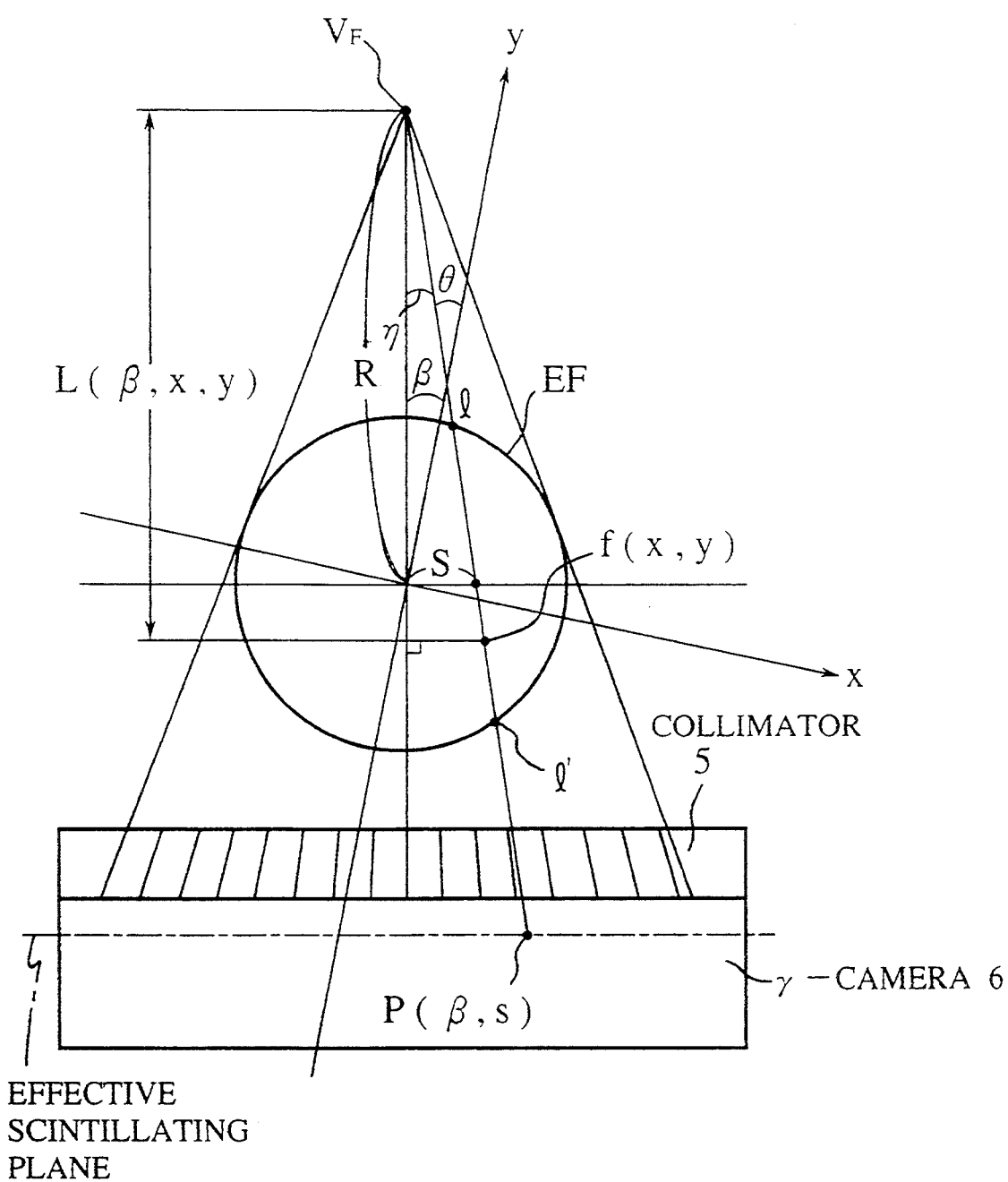
FIG. 2 illustrates a general idea as to how to reconstruct a SPECT image utilizing the fan-beam collimator.

Referring to FIG. 2, when a SPECT image is reconstructed with employment of the fan beam collimator, a geometric positional relationship is established among an effective visual field "EF", the fan beam collimator 5 and a focal point "$V_F$". FIG. 2 shows a geometry of data acquisition using a flat detector with a fan-beam collimator 5. In FIG. 2, symbol "β" denotes an angle of the gamma camera 6 and symbol P(β, S) indicates a projection image along l—l' direction. S denotes a distance between the rotation center of the gamma camera 6, and an intersecting point on l—l' with a parallel line to the effective scintillating plane and passing through the rotation center. R denotes a distance between the focal point $V_F$ of the fan-beam collimator and a rotation center of the gamma camera 6.

When the above-defined geometric positional relationship as shown In FIG. 2 is satisfied, a SPECT value f(x, y) corresponding to the reconstructed image data is expressed by following equation (1).

$$f(x, y) = (1/2\pi) \int_{-\pi}^{\pi} (R/L)^2 \int_{-\infty}^{\infty} \bar{P}(\beta, S) h(t - S) dS d\beta \quad (1)$$

where $\bar{P} = P(\beta, S) \cos \eta$, in which η indicates an angle between a center perpendicular line drawn from the focal point $V_F$ to the a collimator surface, and a line drawn from the focal point $V_F$ to the projection image P(β, S). L indicates a distance between the focal point $V_F$ and a point on the center perpendicular line (drawn from the focal point $V_F$ to the a collimator surface) where the point is an intersection of the center perpendicular line and a perpendicular drawn from the reconstruction point f(x, y) to the center perpendicular line.

In the fan-beam collimator, the spatial resolution is deteriorated as the region in question becomes far from a collimator surface. Therefore, the closer the data to be detected is located to the gamma camera, the better qualified data are obtained. Utilizing the above-mentioned characteristic, in order to obtain the reconstruction images with the high resolution, the filtered data are back-projected in a limited area which is near the collimator excluding a circled region that passes through the focal point $V_F$ and the rotation center O shown in FIG. 3, so that the data are not back-projected in an area which is far away from the collimator where the spatial resolution is deteriorated. Accordingly, the back-projection is carried out by using data whose resolutions are desirably good, so that the high-resolution SPECT images can be obtained. Note that even when the back-projection area is thus limited as described, the back-projection can be consistently performed mathematically by utilizing 180° symmetry of the data.

Figure 3:
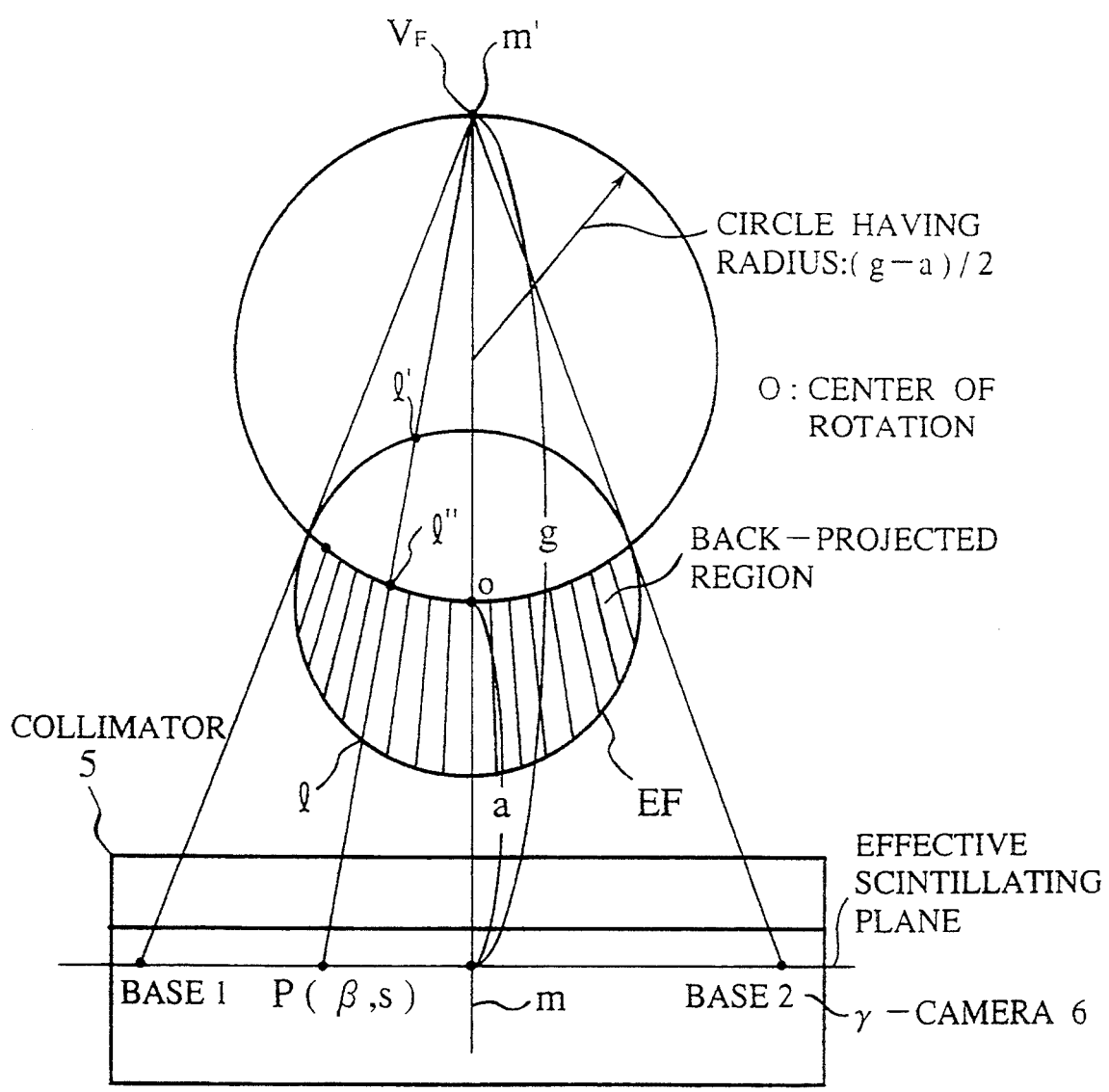
FIG. 3 illustrates a back-projected region according to the SPECT image reconstructing apparatus utilizing a filter function such as the Delta function.

Referring to FIG. 3, convoluted projection data are back-projected to a predetermined reconstructing region which is located near the fan-beam collimator 5, for example, a hatched area in FIG. 3.

Referring still to FIG. 3, projection data are filtered and then backprojected into the area within an isosceles triangle whose vertex is the focal point of the fan beam and whose base (BASE 1 and BASE 2) is the fan-beam collimator surface, and outside a first circle whose diameter is a line connecting $V_F$ to O where O denotes a center of rotation of the gamma camera 6.

More preferably, a second circle with a center thereof being the rotation center O of the gamma camera 6 is generated such that the second circle is inscribed by the isosceles triangle $V_F$-BASE1-BASE2. The predetermined reconstructing region corresponds to the region of the effective field that lies within the second circle and lies outside the first circle. This further preferred predetermined reconstructing region corresponds to the hatched area (back-projected region) in FIG. 3. When a distance between the focal point $V_F$ and the effective scintillating plane is g, and a distance between the center of rotation O of the camera 6 and the effective scintillating plane is a, the radius of the first circle is (g−a)/2. Line m—m' represents the center perpendicular line drawn from the focal point $V_F$ to the the collimator surface or the effective scintillating plane.

Now, a mathematical significance will be briefly described about why the back-projection region is thus limited as the hatched region shown in FIG. 3.

Consider a case where the projection data are acquired by the parallel-beam collimator. In this case, when the region close to the gamma camera is back-projected in a manner that the close region is bounded and separated by a straight line parallel to a gamma camera's detection surface and passing through the rotation center of the gamma camera, it is equivalent to say that the backprojection corresponding to 180° is carried out in every point within the effective view (field of view) after the one-rotation-worth back-projection. In other words, since there are not caused unwanted overlappings in the backprojection region, the artifact is not caused in thus obtained SPECT image. On the other hand, the parallel beam is considered to be such that the focal point of the fan beam is placed on an infinite point. Thus, in a case utilizing the fan-beam collimator, it suffices to perform back-projection over the hatched region shown in FIG. 3.

Thus obtained reconstruction results present significantly high resolution SPECT image data on the condition that the projection data have 180° symmetry. However, as will be described at a later stage in this specification, the projection data obtained by using the fan-beam collimator do not have 180° symmetry. Therefore, as will be described later, the convolution function h(x) is divided into the first convolution function h1(x) and the second convolution function h2(x). The back-projection processes are applied to respective data convoluted with the first convolution function h1(x) and the second convolution function h2(x), respectively. Thereafter, the respectively and separately obtained back-projected data are summed up so as to obtain the final back-projection result. Thereby, there is obtained a further improved image accuracy and resolution.

A novel present invention can be illustrated by that, as will be discussed at a later stage of the specification, the reconstruction filter h(t-S) (see equation (1)) is divided into two convolution functions h1(x) and h2(x).

Hereinbelow, difference between nature of projection data obtained by using a parallel beam collimator and nature of projection data obtained by using a fan beam collimator will be described.

NATURE OF PARALLEL BEAM AND FAN BEAM

Figure 7:
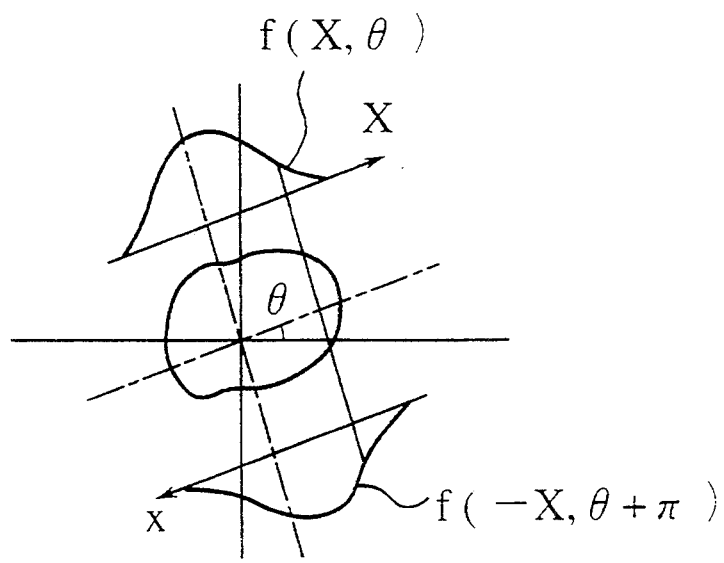
FIG. 7 illustrates a projection example using a parallel beam collimator.

Referring to FIG. 7, when the projection data are obtained by utilizing the parallel beam, projection data f(x, θ) is equal to that obtained 180° opposite thereto. In other words, f(x, θ)=f(−x, θ+π). Then, when the data are convolution-performed using a reconstruction filter h(x), there are obtained equations (2) and (3).

$$q(x, \theta) = f(x, \theta) * h(x) \quad (2)$$

$$q(-x, \theta+\pi) = f(-x, \theta+\pi) * h(x) \quad (3)$$

Hence, q(x, θ)=q(−x, θ+π). Thus, in the convolution-performed data, a 180° symmetric property is held.

Figure 8:
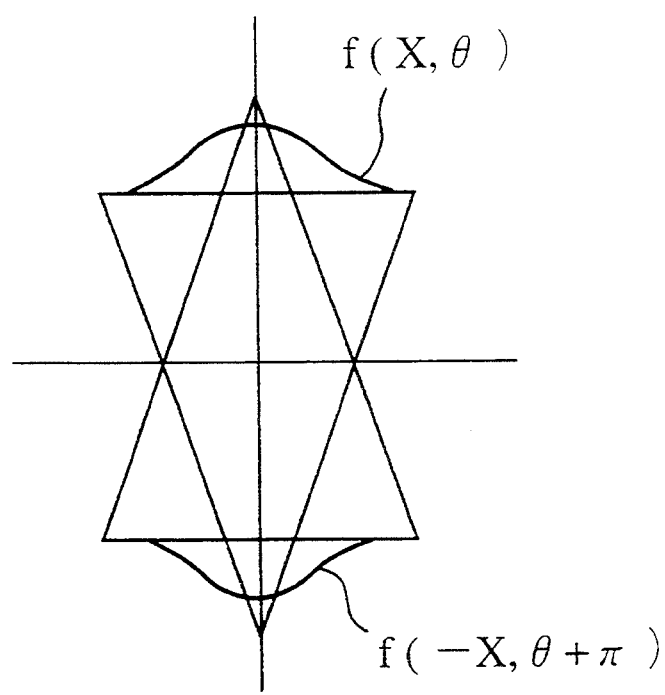
FIG. 8 and FIG. 9 illustrate a projection example using a fan beam collimator.
Figure 9:
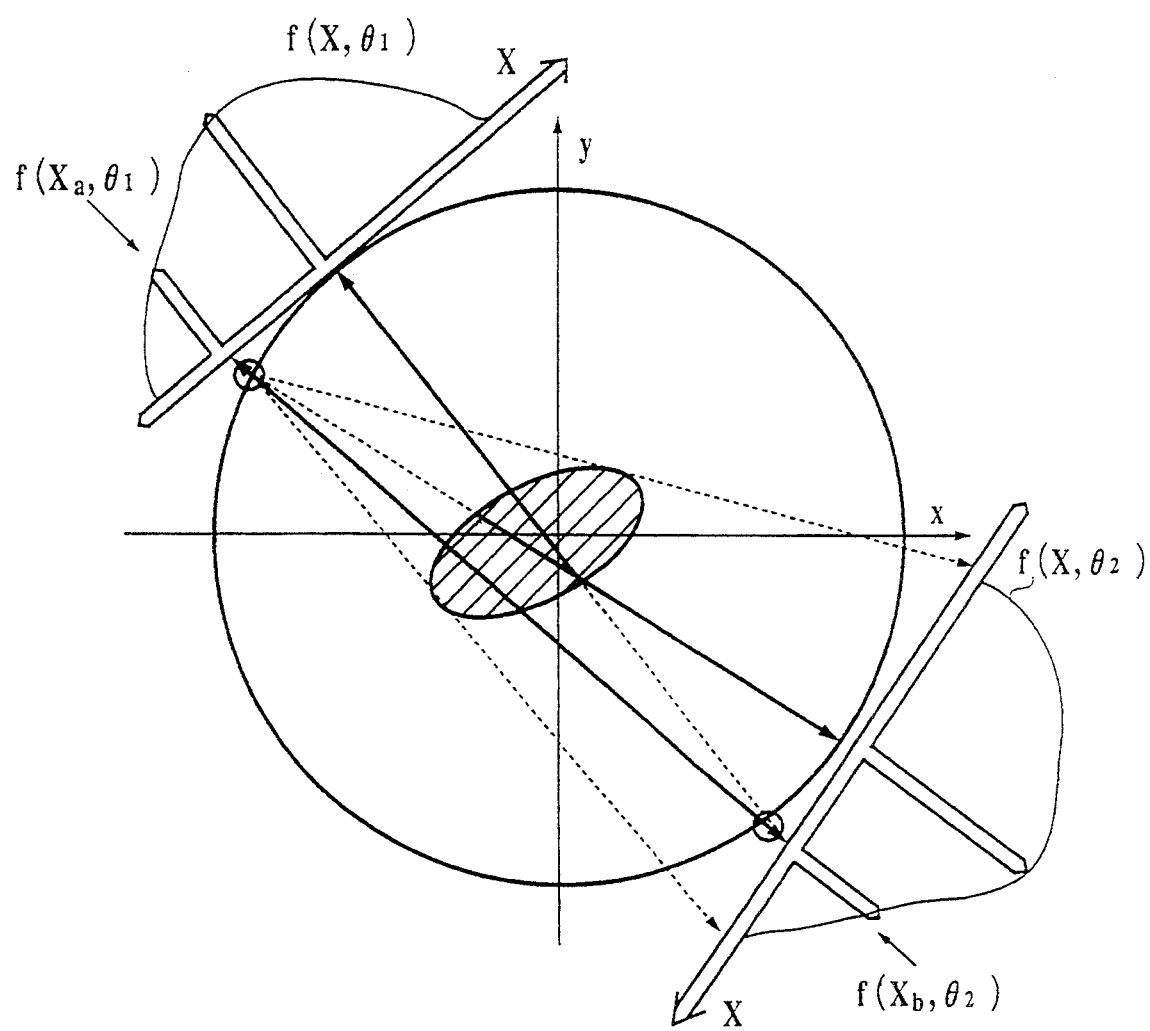

On the other hand, referring to FIG. 8 and FIG. 9, when the projection data are obtained by utilizing the fan beam collimator, f(x, θ) is not equal to f(−x, θ+π), that is, the 180° symmetric property is not held. When the data are convolution-performed using the reconstruction filter h(x), there are obtained equations (4) and (5).

$$Q(x, \theta) = F(x, \theta) * h(x) \quad (4)$$

$$Q(-x, \theta+\pi) = F(-x, \theta+\pi) * h(x) \quad (5)$$

Since F(x, θ) is not equal to F(−x, θ+π), the convolution-performed results (4) and (5) are not equal. Thus, the 180° symmetric property as described in the parallel beam is not held.

In other words, in a case of fan-beam data acquisition apparatus, referring to FIG. 9 there exists another path, in light of a path of a certain projection datum, such that $$F(xa, \theta 1) = F(xb, \theta 2). \quad (6)$$

However, equation (6) does not hold for every x, unlike the parallel-beam system. Now, when convolution is performed with the reconstruction function or filter, there are obtained following equations.

$$Q(x, \theta 1) = F(x, \theta 1) * h(x)$$

$$Q(x, \theta 2) = F(x, \theta 2) * h(x)$$

Since F(xa, θ1)=F(xb, θ2) does not hold for every x, Q(x, θ1) is not equal to Q(x, θ2). Now, h(x) is divided into a portion that can be expressed with a constant times the Delta function (see FIG. 4B, also referred to as a first convolution function hereinafter) and other remaining portion (see FIG. 4C, also referred to as a second convolution function hereinafter). Then, when the projection data are convolution-performed, the portion convoluted with the first convolution can have 180° symmetry.

Next, a property concerning the Delta function will be described. Convolution * is defined to be as such shown in equation (7).

$$f(t) = f_1(t) * f_2(t) \quad (7)$$
$$= \int_o^t f_1(x) \cdot f_2(t - x) dx$$

Convolution with Delta function δ(x) will be expressed with following equation (9).

$$f(t) * \delta(t) = \int_o^t f(x) \cdot \delta(t - x) dx = f(t) \quad (8)$$

where, δ(x)=1 (x=0), and δ(x)=0 (when x is not 0). Here, alternatively, we may adopt a function D(x) such that D(x)=A (x=0) where A is a constant, and D(x)=0 (when x is not 0), in place of the Delta function δ(x).

As seen from equation (8), even if convolution is operated with the Delta function, an original function f(t) is restored as such. Therefore, by forming and approximating the reconstruction filter to the Delta function or constant times the Delta function. A convolution process is carried out without changing an original shape of the projection data.

Figure 4A:
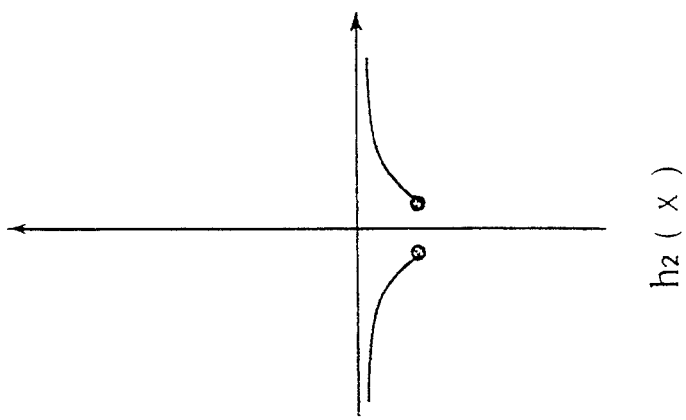
FIGS. 4A-4C illustrates the reconstruction filter function Is divided into two parts comprising the Delta function and the remainder. The reconstruction filter shown in FIG. 4A is divided into a function h1(x) (FIG. 4B) which provides a constant value when x=0 and provides 0 when x is not 0, such as Delta function, and a h2(x) (FIG. 4C) as a remainder of FIG. 4A.
Figure 4B:
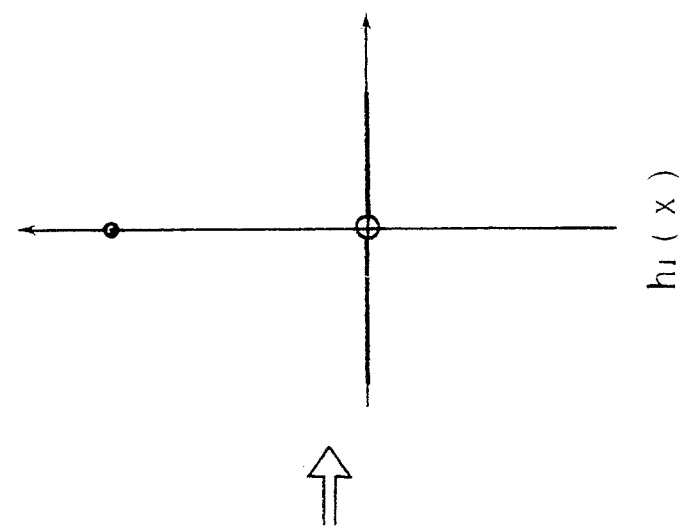
Figure 4C:
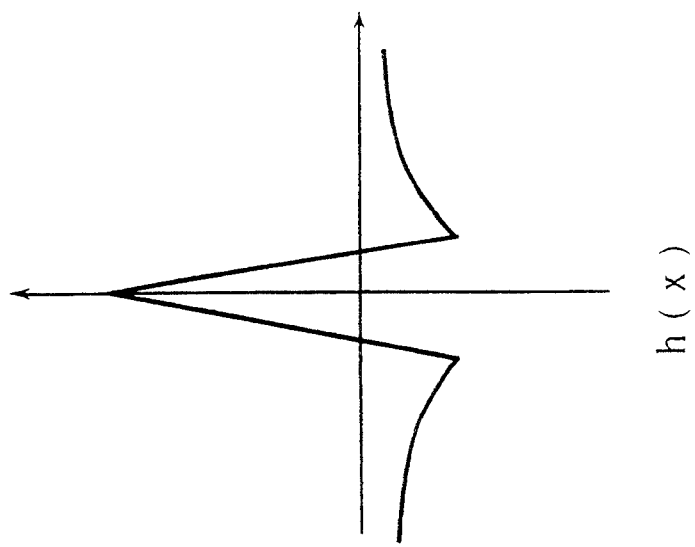

For example, when the characteristic of the reconstruction filter is h(x) shown in FIG. 4A, the h(x) can be divided into two parts comprising the first convolution function h1(x) and the second convolution function h2(x) shown in FIG. 4B and FIG. 4C since a neighborhood of an origin area can be approximated to a constant multiply of the Delta function. In other words, h(x)=h1(x)+h2(x). Moreover, since the convolution satisfies a distribution law, the convolution may be separately performed on h1(x) and h2(x), namely, equation (9) holds.

$$
\begin{aligned}
P(x, \theta) * h(x) &= P(x, \theta) * \{h1(x) + h2(x)\} \\
&= P(x, \theta) * h1(x) + P(x, \theta) * h2(x) \\
&= A \cdot P(x, \theta) + P(x, \theta) * h2(x),
\end{aligned}
\quad (9)
$$

where A is some constant.

Now, since the first term $A*P(x, \theta)$ of equation (10) possesses the 180° symmetric property, the data corresponding thereto can be reconstructed by the above technique involving equation (1) where the fan-beam data are back-projected in a limited region in sufficiently close vicinity of the fan-beam collimator as shown in FIG. 3. On the other hand, since the second term $P(x, \theta)*h2(x)$ does not present the 180° symmetric property, an accurate SPECT image can not be obtained by back-projecting to the region close to the collimator. Hence, as for the second term, it is preferred to carry out back-projection in a whole range of the SPECT field of view. In other words, the data which are filtered by using the second convolution function h2(x) are back-projected into the whole range of the SPECT field of view.

Then, the respectively back-projected results based on the first and second convolution functions corresponding to the first and second terms of equation (9) are mathematically summed up. Thereby, the final back-projection result is obtained, so that the SPECT image in accordance with the back-projection results is reconstructed.

As have been described, according to the present invention, the reconstruction filter is divided into the first convolution function and the second convolution function, and the projection data are respectively convolution-performed by the first and second convolution functions. The result convoluted (filtered) by the first convolution function is back-projected in a limited region of the close vicinity of the collimator, and the result convoluted (filtered) by the second convolution function is back-projected into the whose range of the SPECT field of view. Thereby, there is obtained an accurate SPECT image with a significantly high resolution.

Figure 5A:
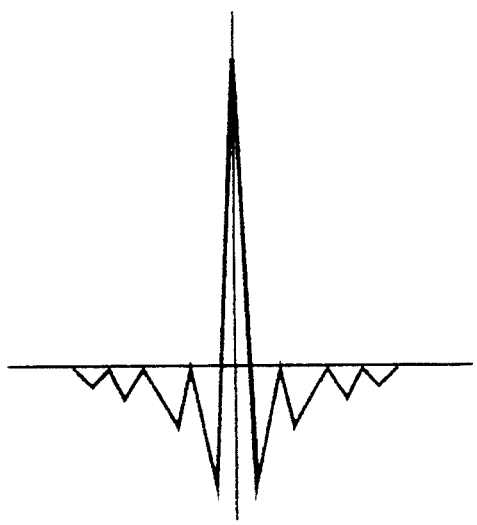
FIGS. 5A-5C show various reconstruction filter functions (convolution functions).
Figure 5B:
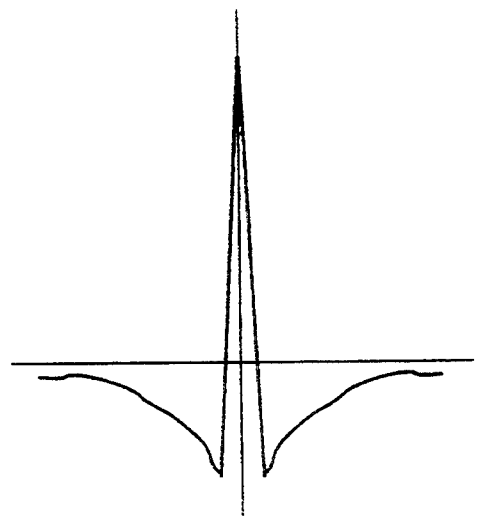
Figure 5C:
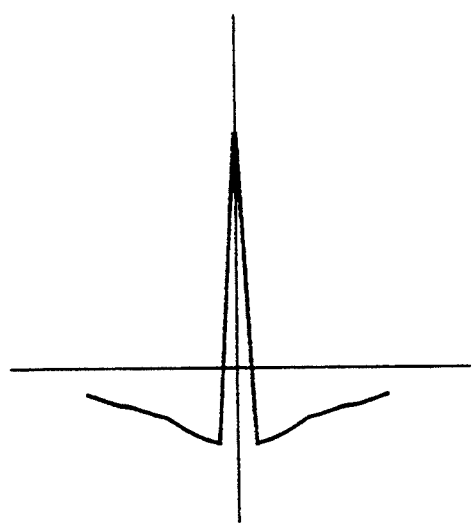

The reconstruction filter function (convolution function) which will be divided into two parts may be as ones shown in FIG. 5A-FIG. 5C, for example. FIG. 5A is a filter that is better known as a RAMP filter which gives a high resolution but is weak against a noise so that an image obtained thereby is likely to be unstable. FIG. 5B is a filter that is better known as Shepp & Logan filter in which a high-frequency component is removed from the Ramp filter, and which has a high tolerance against the noise so that the image obtained thereby is stable. FIG. 5C is a filter that is better known as Chesler filter in which the high-frequency component is further removed from the Shepp & Logan filter, and which is suitable for data having a great deal of noises therein.

Figure 6A:
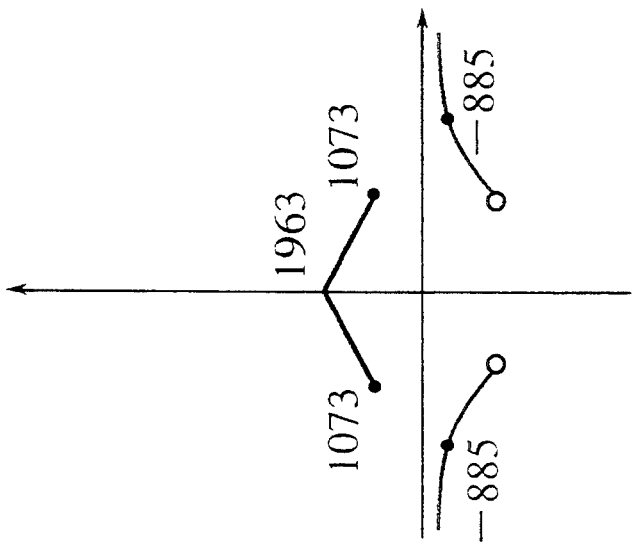
FIGS. 6A and 6B show another examples for filter values to be employed in order to further improve the image resolution.
Figure 6B:
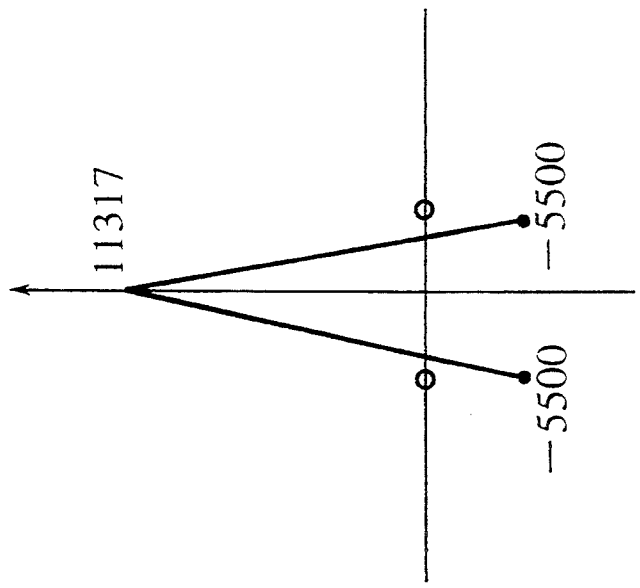

In order to further improve the resolution, referring to FIG. 6A and 6B, there may be employed a filter shown in FIG. 6A and FIG. 6B which is made in light of the image degradation or blurriness. FIG. 6A is a main filter (corresponding to the h1(x) discussed above) and FIG. 6B is a sub-filter (corresponding to the h2(x)) for the filter.

In summary, in order to reconstruct and obtain a best-qualified SPECT image, in the present invention, the SPECT image reconstruction steps includes at least the following two steps I and II:

I. Backprojection after convolution-performed by the first convolution function h1(x) such as an approximation equation of delta function; and II. Backprojection after convolution-performed by the second convolution function h2(x).

For the filtered projection data using the convolution function hi(x) such as the approximation equation of Delta function, it is back-projected in the following manner. That is, a range for the back-projection is defined with respect to respective pixels of reconstructed image present at a side near the fan-beam collimator 5 within an effective visual field of the gamma camera 6, as shown in FIG. 3.

In above step II, another set of projection data are filtered by using the function h2(x) in a manner that data are backprojected into a whole range of the SPECT field of view.

Thereafter, the back-projected results based on the first and second terms of (9) are mathematically summed up to obtain final back-projected data. In other words, the backprojected data after convolution-performed by using the first convolution function h1(x) such as the approximation equation of delta function (I) and another backprojected data after convolution-performed by using the second convolution function h2(x) (II) are summed up for each pixel to form and reconstruct the SPECT image.

In other words, projection data are acquired for 360°. The acquired projection data are filtered by using the first convolution function h1(x) such as an approximation equation of delta function. The h1(x)-filtered data are backprojected in a manner that the fan-beam data are back-projected In a region corresponding to a sufficiently close vicinity of the fan-beam collimator surface. Another projection data are acquired for 360°. The another projection data acquired are filtered by using the second convolution function h2(x). The h2(x)-filtered another projection data are backprojected into a whole range of the SPECT field of view. Those two backprojected data are summed to obtain and reconstruct the final SPECT image (I plus II) with utmost accuracy and high spatial resolution.

Besides those already mentioned above, many modifications and variations of the above embodiments may be made without departing from the novel and advantageous features of the present invention. Accordingly, all such modifications and variations are intended to be included within the scope of the appended claims.

What is claimed is:

1. A single photon emission computed tomography (SPECT) apparatus in which a distributed image of a radio isotope injected into a biological body under medical examination is reconstructed along with a tomographic plane, the apparatus comprising:

detector means, including a fan-beam collimator, for detecting gamma ($\gamma$) rays emitted from the radio isotope;

means for effecting relative rotation between the biological body and the detector means about a center of rotation to thereby acquire projection data from a different direction;

first reconstructing means for convoluting the projection data obtained from the detector means, by a first convolution function, and for back-projecting the first convoluted projection data to a specific region which lies in a sufficiently close vicinity of the detector means;

second reconstructing means for convoluting the projection data by a second convolution function, and for back-projecting the second convoluted projection data to another specific region; and display means for displaying thereon a distribution image reconstructed by the first and second reconstructing means.

2. The apparatus of claim 1, wherein an approximation equation of a delta function serves as the first convolution function.

3. The apparatus of claim 1, wherein the another specific region in the second reconstructing means corresponds to a whole range of a field of view of the detector means.

4. The apparatus of claim 1, wherein the specific region in the first reconstructing means corresponds to a region excluding an area encompassed by a first circle passing through a focal point of the fan-beam collimator and having a diameter equal to the distance between the focal point of the fan-beam collimator and the center of rotation.

5. The apparatus of claim 4, wherein the specific region in the first reconstructing means corresponds to a region of an isosceles triangle whose vertex is a focal point of the fan-beam collimator and whose base is a surface of the detector means, and which excludes the first circle.

6. The apparatus of claim 5, wherein the specific region in the first reconstructing means corresponds to a region of a second circle which is inscribed by the isosceles triangle and which lies outside the first circle.

7. A method for reconstructing a single photon emission computed tomography (SPECT) image of a distribution of a radio isotope injected into a biological body in a nuclear medical examination system using a fan-beam detecting means, the method comprising the steps of:

(i) detecting gamma-rays emitted from the radio isotope so as to obtain projection data, by the detecting means in a fan-beam form around the biological body with respect to a rotation center for 360°;

(ii) firstly performing a first convolution operation between the projection data and a first convolution function, and then backprojecting a result of the first convolution operation in a manner that a backprojecting region corresponds to an effective field which lies in a sufficiently close vicinity to the detecting means;

(iii) secondly performing a second convolution operation between the projection data and a second convolution function, and then backprojecting a result of the second convolution operation to another reconstruction region; and (iv) obtaining the SPECT image in accordance with backprojection results obtained in step (ii) and step (iii).

8. The method of claim 7, wherein an approximation equation of a delta function serves as the first convolution function.

9. The method of claim 7, wherein the reconstruction region in step (iii) corresponds to a whole range of a field of view of the detecting means.

10. The method of claim 7, wherein the firstly performing a first convolution function step (ii) includes the steps of:

convoluting the projection data to obtain convoluted projection data, by using an approximation equation of delta function; and executing a back-projection for the convoluted projection data to the effective field, wherein the effective field is determined in a manner comprising the steps of:

locating a focal point of the fan-beam detecting means;

drawing lines to both end points of a surface of the fan-beam detecting means from the focal point so as to form an isosceles triangle;

generating a first circle passing through the focal point and whose diameter is a line connecting the focal point and the center of rotation of the detecting means;

generating a second circle with a center thereof being the rotation center of the detecting means such that the second circle is inscribed by the isosceles triangle; and defining the region of the effective field that lies within the second circle and lies outside the first circle.

* * * * *